United States Patent [19]

Happel et al.

[11] 4,320,030

[45] Mar. 16, 1982

[54] PROCESS FOR MAKING HIGH ACTIVITY TRANSITION METAL CATALYSTS

[75] Inventors: John Happel, Hastings-on-Hudson, N.Y.; Miguel A. Hnatow, Caldwell, N.J.

[73] Assignee: Gas Research Institute, Chicago, Ill.

[21] Appl. No.: 132,536

[22] Filed: Mar. 21, 1980

[51] Int. Cl.³ .................... B01J 21/02; B01J 27/04; B01J 27/24

[52] U.S. Cl. .................... 252/432; 252/438; 252/439; 518/714

[58] Field of Search ............ 252/438, 439, 432; 518/714, 728

[56] References Cited

U.S. PATENT DOCUMENTS

| | | | |
|---|---|---|---|
| 2,490,488 | 12/1949 | Stewart | 518/714 |
| 3,663,431 | 5/1972 | Wagner | 252/439 X |
| 3,764,649 | 10/1973 | Kurtak et al. | 423/56 |
| 3,876,755 | 4/1975 | Kurtak et al. | 423/517 |
| 4,199,439 | 4/1980 | Gatsis | 252/439 X |

*Primary Examiner*—W. J. Shine

[57] ABSTRACT

A catalyst particularly useful in conversion of $CO-H_2$ mixtures is prepared by preparing an intimate mixture of a compound containing molybdenum, vanadium and/or tungsten or a mixture of two or more of the said molybdenum, vanadium, and tungsten compounds in a melt of ammonium thiocyanate-thiourea, or a mixture of the two, heating the melt in a non-oxidizing atmosphere at temperatures sufficient to evolve gases for a time to convert the melt to a solid mass, calcining the solid in an inert atmosphere to prevent over reduction, and then passivating the catalyst, after cooling with inert gas, with a very dilute stream containing oxygen, until no further exotherm is noted. The mass may be broken up, or ground and pelletized, in process as desired for convenience in handling, and the product is desirably further heated in this fashion.

6 Claims, No Drawings

PROCESS FOR MAKING HIGH ACTIVITY TRANSITION METAL CATALYSTS

FIELD OF THE INVENTION

The invention relates to a novel method for production of catalysts from Group V and VI transition metals.

BACKGROUND OF THE INVENTION

Catalysts based on these elements find wide application in the processing of hydrocarbon feed stocks. They may be employed in treating material derived from other fossil fuels such as coal as well as from petroleum sources.

Most hydrodesulfurization and hydrotreatment catalyst contain cobalt and molybdenum deposited on an alumina carrier. Such catalysts have also been employed for conducting methanation, production of hydrocarbon by the Fischer-Tropsch synthesis, denitrogenation, hydroforming, hydrocracking, coal liquefaction and the water gas shift reaction. In some formulations nickel and molybdenum have been employed as well as nickel and tungsten, and in some cases other supports containing such materials as silica. Vanadium oxide catalysts supported on various carriers have also been found to be active in promoting the above types of hydrocarbon conversions.

After having been charged into an industrial reactor the catalysts are often activated by a sulfur-containing reducing atmosphere and remain in contact with sulfur and reducing substances during their entire life. There is evidence of considerable reaction of the transition metals in these catalysts with sulfur. However, the various forms of lattice and surface sulfur present on the working catalysts, and their involvement in the actual reactions such as hydrodesulfurization is not entirely understood. A considerable proportion of the oxygen bound to the transition metals, however, remains uncovered to sulfide and it has been suggested in the case of molybdenum that a binding to both oxygen and sulfur is required for optimum performances.

In some cases the transition metals are employed alone without addition of other materials described as supports and promoters. In the past a method of preparing molybdenum and tungsten sulfide catalysts by decomposition of thiosalts has been employed. For this purpose the thiosalts are first prepared by precipitation from ammonium salt of the acid of the molybdenum or tungsten by hydrogen sulfide. The thiosalts are then decomposed in an atmosphere of hydrogen. See Kurtak et al U.S. Pat. Nos. 3,764,649 and 3,876,755. There is some evidence that in the course of this thermal decomposition the sulfides $MoS_3$ or $WS_3$ are first formed and that they then decompose to a non-stoichiometric sulfide containing close to two sulfur atoms, i.e., $MoS_2$ or $WS_2$. Thus, in the formation of these catalysts the active compound is formed by removal of excess sulfur as contrasted to the procedure in which one starts with oxide which is later converted to sulfide. In the latter case it appears that the oxide form $MoO_3$ is the initial stable oxide form and that this is converted to the dioxide in a reducing atmosphere before being converted to the corresponding disulfide. Catalysts based on transition metal compositions and involving supports can also be prepared from the thiosalts. In use, a portion of the sulfide form is converted to oxide when one starts initially from a pure sulfide type catalyst.

In catalysts containing vanadium the stable higher oxidation state corresponds to a pentavalent form $V_2O_5$ instead of $MoO_3$ and $WO_3$. The sulfide $V_2S_5$, analogous to the unstable $MoS_3$ and $WS_3$, is also unstable and can be decomposed to $V_2S_3$ corresponding to $MoS_2$ and $WS_2$. The active form of vanadium sulfide thus corresponds to a non-stoichiometric composition close to trivalent vanadium.

U.S. Pat. No. 4,151,190, "Process for Producing $C_2$–$C_4$ Hydrocarbons from Carbon Monoxide and Hydrogen," Craig B. Murchison and Dewey A. Murdick, gives a listing of references pertinent to the development of molybdenum and tungsten catalysts. In addition, the book *Sulfide Catalysts—Their Preparation and Application*, Otto Weisser and Stanislov Landa, Pergamon Press, N.Y. 1973, gives details concerning the preparation of catalysts in which one initially obtains a higher sulfide, which is subsequently converted to a lower valent modification.

In addition to catalyst preparation by impregnation on a carrier and decomposition of a solid material, catalysts of this type have sometimes been prepared by coprecipitation from organic solutions. The impregnation technique has, however, been most frequently employed though it has the disadvantage that some type of activation is usually necessary to obtain the desired active catalyst form. An additional disadvantage is the fact that the high surface area of the support does not always contribute to the production of a catalyst with a high surface area of the active components, since subsequent activation reactions change the nature and aggregation of the starting materials which have been deposited on the support.

In the case of precipitation, the preparation of the thiosalts is inconvenient and expensive since precipitation from dilute solution is required and considerable time is occupied in the process (see, for example, P. Rainasamy and A. J. Leonard, J. Cat. 26, 352 (1972). In addition, vanadium sulfide cannot be conveniently prepared by this procedure. Also it is difficult to incorporate other components into the catalyst in an intimately mixed condition.

OBJECTS OF THE INVENTION

Accordingly, it is an object of the present invention to provide means for preparing a catalyst with the desired oxide to sulfide ratio required for optimum performance.

Another object is to produce a high surface area catalyst in which the active area is obtained directly rather than by the impregnation of active materials on a high surface area support.

Another object is to employ a procedure whereby mixed transition and other metals may be readily incorporated into the catalyst material in finely subdivided form conducive to chemical interaction.

Another objective is to enable incorporation of such elements as carbon and nitrogen which in some cases may serve to improve catalyst activity.

Further objectives will be apparent from the detailed description and application of the invention.

SUMMARY OF THE INVENTION

In accordance with the present invention, we obtain the above desired objects by preparing a molten solution of a catalyst metal compound—most preferably a molybdenum, tungsten or vanadium compound—in molten ammonium thiocyanate and/or its isomer thiourea, heating said mixture in a non-oxidizing atmosphere to a temperature sufficient to produce brisk evolution of gases (about 170° C.) and continuing the heating while raising the temperature (to the 200°–300° C. range) till the mass finally solidifies, calcining the mass in an inert atmosphere at temperatures sufficiently high, preferably to 400°–600° C., to remove hydrogen sulfide or sulfur, and finally further heating in a reducing atmosphere to activate the catalyst. The resultant product is cooled in a stream of non-reactive gas and is passivated with a stream of gas containing oxygen and/or steam, diluted with nitrogen, until no further exotherm is noted at low temperatures.

For convenience in handling, the solidified mass is preferably broken up into small pieces, or ground and pelletized for calcination. This is preferably done after an intermediate heating at 200°–300° C. to condition the mass for grinding. The passivated product is preferably again ground and pelletized.

DESCRIPTION OF THE PREFERRED EMBODIMENTS

The present invention is based on the discovery that ammonium thiocyanate is a good solvent for various transition metal salts and that as it decomposes, transition metal compounds are produced which contain oxygen and sulfur primarily. Upon further reductive decomposition these materials are converted to high surface area materials with catalytic properties for a number of reactions characteristic of those employed in petrochemical and petroleum refining applications of transition metals in reducing environments.

Ammonium thiocyanate ($NH_4CNS$) is a colorless salt which crystallizes in anhydrous plates which rapidly absorb moisture upon exposure to air. It is very soluble in water, alcohol and acetone and melts with little decomposition at 159° C. It is an isomer of thiourea ($(NH_2)_2CS$) and at 170° C. isomerization proceeds fairly readily with the production of about 25% thiourea in equilibrium with the thiocyanate. The eutectic point of the equilibrium mixture is 103° C. As the temperature is increased to 190°–200° C., more rapid decomposition occurs with evolution of hydrogen sulfide, ammonia and carbon disulfide, leaving guanidine thiocyanate ($CH_5N_3NCNS$) in the residue.

Ammonium thiocyanate forms corresponding thiocyanates when reacted with compounds of a number of metals and many of these materials form salts which are miscible with the ammonium thiocyanate. Organic bases such as guanidine and pyridine may be substituted for ammonia in the formation of metal cations containing complexes. A large variety of such compounds has been reported in the case of molybdenum thiocyanate. For example, dipyridinium molybdenum dioxytrithiocyanate $(C_5H_6N)_2 MoO_2(CNS)_3$ can be prepared from ammonium thiocyanate. This compound melts at 181° C. and thus would be miscible with molten ammonium thiocyanate at that temperature. Various thiocyanates have been reported for tungsten, vanadium and chromium as well as for nickel and cobalt. For more details concerning these compounds see *Cyanogen Compounds—Their Chemistry, Detection and Estimation* by Herbert E. Williams, Eduard Arnold Co., London, 2nd Edition.

We have discovered that when a mixture of salts of various metals preferably vanadium, tungsten and molybdenum together with other desirable compounds such as pyridine, silica gel or carbon black is added to an organic solution of ammonium thiocyanate and the solution is evaporated, a molten mixture results in which all the ingredients are intimately in contact with each other. Alternatively the salts may be added directly to molten ammonium thiocyanate or thiourea.

The mixture is stirred continuously while heating and most of the water is evolved at a temperature below 170° C. When this temperature is reached, decomposition starts and the mixture evolves various gases including sulfur dioxide and carbon monoxide. As the temperature is further increased to about 200°–300° C. and maintained at a temperature, preferably between 250°–270° C., the mixture becomes viscous and finally solidifies to a black solid. The mass is then placed in an oven under an inert or otherwise non-oxidizing atmosphere and maintained at a temperature of 250°–450° C., preferably 300°–350° C., for a period of 2–20 hours, preferably about 3 hours. The solid mass is then cooled, crushed and sieved.

The sieved mass crushed to particles of up to ¼ inch in size, preferably 30–60 mesh, is charged to a calcining furnace and heated for a period of time between 178 hour and 4 hours, preferably about 1 hour by means of a stream of nitrogen to the desired reduction temperature, 400°–600° C. and preferably 450°–550° C. When the desired reduction temperature is reached, the nitrogen stream is changed to a stream containing either pure hydrogen or a mixture of hydrogen and nitrogen.

Alternatively the bed may be rapidly heated by hydrogen over a period of for 5–30 minutes, preferably for 15 minutes. If this heating with hydrogen is not conducted sufficiently rapidly, reduction of the catalyst mass may occur too slowly resulting in a lower activity catalyst. Therefore, it is preferable to first heat the mass with nitrogen, and during this preliminary heating period little decomposition of the mass occurs.

It has been found that most of the hydrogen sulfide evolution occurs shortly after introduction of hydrogen into the heated catalyst mass, using the proposed embodiment of the invention in which the mass is first heated with nitrogen. During this period it has also been found desirable to maintain a small concentration of $H_2S$ in the hydrogen reduction stream. Concentrations of from 0.06–1.0 vol.% of $H_2S$ have been found suitable, and preferably between 0.1–0.2 vol.%. If no $H_2S$ is maintained in the hydrogen stream, the sulfide content of the catalyst mass is reduced too much and in the case of molybdenum, formation of the metal may result. This can be avoided by using a calcining time not exceeding 5 hours and preferably between 1–2 hours. Unfortunately, in some cases this period of time is not sufficient to completely remove all volatile decomposition products such as sulfur, thiocyanate and hydrocarbons. As a result, the catalyst mass can, after reduction, contain materials which plug up catalyst equipment and back pressure regulators during subsequent catalyst use. Therefore, the proposed procedure is to conduct the reduction with a hydrogen atmosphere containing $H_2S$ over a long enough period of time to not only obtain the proper degree of sulfur removal but also to remove all extraneous volatile components. This usually occupies from 2–10 hours, and preferably 4–5 hours.

Following reduction, which involves considerable shrinkage, the catalyst mass is cooled in a stream of nitrogen. It is important at this point to passivate it before exposure to the atmosphere. This is accomplished by passing a dilute mixture of oxygen and/or water in nitrogen over the catalyst for a sufficient period of time until no appreciable temperature rise in the catalyst bed is noted. If this is not done, many of the catalysts prepared, especially those containing vanadium, are highly pyrophoric and will glow when removed from the reduction reactor. This high temperature is due to oxidation and results in the destruction of both the desirable active sulfide state of the catalyst and loss of surface area due to sintering.

After the catalyst is passivated it is removed from the reduction chamber and processed further. It may be powdered and then compressed to produce granules or pellets for use in appropriate catalytic processes.

In order to determine whether the active form of catalyst was only sulfide or whether oxygen is also involved, a series of experiments was conducted in which the proportion of molybdenum to sulfur in the original molten thiocyanate mixture varied, since in our case the only form of sulfur addition is derived from thiocyanate decomposition. The resulting catalyst was evaluated using a mixture of CO and hydrogen containing gases blended to resemble a typical synthesis gas produced by coal gasification. In this case the primary product is methane. With other operating conditions and different feedstocks, other products could be produced. The objective of the study was to evaluate the effect of catalyst preparation procedures on the catalyst properties by means of a typical reaction, rather than to investigate different processes.

Details of some experiments performed are given to Examples 1–4 and are discussed here to exhibit the fact that suitable catalysts may have both sulfur and oxygen atoms attached to the metal components of the catalyst. The effect of varying the ratio of thiocyanate sulfur to molybdenum is summarized in Table 1. In view of the fact that transition metal thiocyanates exist, it was thought that the precursor to active compound formation might in the case of molybdenum be represented by a hexavalent molybdenum salt $Mo(CNS)_6$. Decomposition of such a material during preliminary heating before calcination could result in formation of $MoS_3$ which upon high temperature calcination could decompose to $MoS_2$. In order to test the validity of such a sequence, several initial mixtures were prepared, corresponding to atomic ratios of S/Mo=6/1, 3/1 and 2/1. $H_2S$ evolved during the hydrogen reduction period following original heating to 500° C. was measured by precipitation of cadmium sulfide. Assuming that very little molybdenum is volatilized relative to $H_2S$ during reduction, it is possible to calculate the atoms of sulfur evolved per atom of molybdenum present. In the case of the S/Mo=6/1 it was found that approximately one atom of S was eliminated as $H_2S$ for each atom of molybdenum present. However, in the case of S/Mo=3/1 only half an atom of S is removed for each atom of Mo present and the same holds true in the case of an initial S/Mo ratio of 2/1. In all cases catalyst activity remains the same. In the case of initial S/Mo-2/1, there is only enough sulfur present to form $MoS_2$ even if all the sulfur in the thiocyanate reacts with molybdenum. Since it can be seen in Table 1 that considerable sulfur is being removed during the reduction it is clear that the active catalyst formed contains less sulfur than corresponds to $MoS_2$ and therefore Mo-O bonds are also necessary to satisfy stoichiometry.

In Example 4 molybdenum sulfide $MoS_3$ was prepared from ammonium thiomolybdate as described by Moldarski, et al. (J. Gen.Chem. (USSR)3, 603 (1933). Similar preparations of thiomolybdate cluster compounds are described by U.S. Pat. Nos. 3,764,649 and 3,876,755 of C. R. Kurtak and D. L. Hartzig. U.S. Pat. No. 3,876,755 describes how ammonium polythiomolybdate may be decomposed by heating to $MoS_2$, which material was noted is useful as a lubricant and as a catalyst. In Example 4 it is shown that approximately 1 mol of sulfur is removed by calcining the thiomolybdate salt. Presumably $(NH_4)_2MoS_4$ upon heating first decomposed to $MoS_3$ upon calcination at higher temperature. The activity of this material as a catalyst is also reported. It appears that it contains substantially more sulfur per molybdenum atom than many of the catalysts prepared according to the present invention, so the catalyst activity is also a function of the surface and lattic structure.

TABLE 1

| | | Reduction of Mo Catalysts | | | |
|---|---|---|---|---|---|
| Initial Ratio of S/Mo | Gm At. Mo | Gm At. S Removed by Reduction | Surface Area $m^2/g$ | | Activity* % CO Conversion |
| | | | new | used | |
| 6:1 | 0.057 | 0.06 | 15.1 | 28.4 | 63 |
| 3:1 | 0.060 | 0.03 | 33.0 | 99.0 | 65 |
| 2:1 | 0.079 | 0.04 | 3.8 | 97.4 | 66 |
| $(NH_4)_2MoS_4$ | 0.077 | 0.07 | 9.4 | 24.7 | 62 |

*Activity measured at 200 psig, 4800 v/v/hr, 550° C.

Another aspect of catalysis by the layered metal dichalcogenides is that their activity as catalysts seems to be associated with random highly disordered morphology (see, for example, R. R. Chianelli, et al. Science 203, 1105 (1979)). It is believed that poorly crystalline $MoS_2$ has improved catalytic activity as compared with the more regular structures which are formed at higher temperatures (P. Rainasamy et al., J. Phys. Chem. 77, 2242 (1973)). The prevention of crystal formation can be aided by the presence of impurities such as silica or carbon and by the preparation of mixed sulfides which will form solutions in the same way that glasses are formed by solid solutions of similar silicates. Several examples in the following show that high activity catalysts can be prepared with such additions and mixtures. Such catalysts should form large stable crystalline forms of $MoS_2$ less readily and thus retain activity for a longer time at elevated temperatures.

Another advantage of the procedure described in this invention is that it is easy to incorporate smaller proportions of other metallic promoters such as nickel or cobalt which are commonly employed in Fischer-Tropsch and hydrodesulfurization catalysts. These materials can be added in the form of organic salts, such as preferably oxalates or acetates, although nitrates can also be employed. Usually, vanadium is added as the soluble vanadium oxalate salt. Molybdenum and tungsten are added as molybdates or tungstates.

SPECIFIC EXAMPLES OF THE INVENTION

The following examples will serve to illustrate the items discussed above.

EXAMPLE 1

The following method of preparation of a 6/1=S/Mo initial mix was employed.

A solution containing 88 g of $(NH_4)_6Mo_7O_{24}\cdot 4H_2O$ in 120 g of distilled water was mixed with a solution containing 228 g of $NH_4CNS$ in 140 g of distilled water. The mixture was heated, evaporating the water and finally decomposing and reacting the salts; the hot residue was cooled to room temperature in a dessicator overnight.

After initial heating the mass was broken into particles of about 30–60 mesh in size and charged to a reactor consisting of a stainless steel tube 1 inch in diameter. 22.2 gm of the mixture, containing 0.057 atoms of molybdenum were charged to the reactor. The system was heated over a period of 1 hr. by passing a stream of 800 cc/minute of nitrogen at a temperature of 500° C. through the mass. At that time the gas flow was switched to a stream of hydrogen at the same volumetric rate of flow. Initially the $H_2S$ content of exit gases was about 15,000 ppm. After a period of 3 hrs. the concentration dropped to 2,200 ppm at which time the flow of hydrogen was stopped and cool nitrogen was passed through the bed for 1 hr., followed by passage of a stream containing 0.1% $O_2$ in nitrogen until no appreciable rise in temperature of the bed could be detected. The product was removed, powdered and a large pellet was prepared by compression of the powder. This mass was broken and sieved to a size of 30–60 mesh. During the reduction period 9.2 g of cadmium sulfide precipitate was formed by passing the effluent gas through a solution of cadmium sulfate. This corresponds to 0.06 atoms of S in the evolved gas as discussed on page 8, line 29. Thus, approximately one atom of sulfur was evolved for each atom of molybdenum present in the charge to the reduction reactor.

The methanation reaction was carried out by passing a mixture of the reactant gases upward through a fixed bed reactor consisting of a stainless steel tube 1 inch in diameter and 14″ in length. The feed gas mixture was preheated by a resistance heater surrounding the tube. Two additional resistance heaters were used to control temperature in the reactor. Pressure was controlled by a back pressure regulator on the exit stream. Exit gases were analyzed on a Perkin Elmer Model 900 Gas Chromatograph equipped with a temperature programmer. Components analyzed include CO, $CO_2$, $CH_4$, $H_2O$, $H_2$ and $C_2$ and $C_3$ hydrocarbons.

5 cc of the catalyst were charged to a catalyst evaluation system. Gas was passed into the reactor at a rate of 4800 v/v/hr. (NTP). Feed gas composition corresponded to the following:

|  | Vol. % |
| --- | --- |
| $H_2$ | 45.4 |
| CO | 39.5 |
| $CH_4$ | 15.1 |

In addition the feed contained 1,300 ppm of $H_2S$ to maintain the catalyst in sulfide state. The $CH_4$ is added to avoid sudden rise in temperature of the catalyst. It acts as a diluent to partially absorb heat produced by the highly exothermic methanation reaction.

At a temperature of 530° C. and reactor pressure of 200 psig the exit gas composition on a dry basis was found to be as follows:

|  | Vol. % |
| --- | --- |
| $H_2$ | 17.9 |
| CO | 22.1 |
| $CH_4$ | 46.7 |
| $CO_2$ | 13.3 |

Calculation based on a carbon balance indicates that this corresponds to a CO conversion of 63% of the CO present in the feed. 64% of the CO converted appears as methane, the remainder being converted to $CO_2$.

EXAMPLE 2

A run was conducted in which an initial mixture corresponding to 3/1=S/Mo was employed. The following materials were used.

A solution containing 88 g of $(NH_4)_6Mo_7O_{24}.4H_2O$ in 120 g of distilled water was mixed with a solution containing 114 g of $NH_4CNS$ in 70 g of distilled water, and processed further as in Example 1.

The procedure for reduction of catalyst was similar to that employed in Example 1. In this case, 16.4 g of a mixture containing 0.060 g at. of molybdenum was charged to the reduction reactor. The evolution of $H_2S$ during reduction corresponded to a precipitate of CdS amounting to 3.82 g which is equivalent to 0.03 g at. of sulfur as discussed on page 9, line 1. Thus, in this case only half an atom of sulfur was evolved for each atom of molybdenum in the reactor.

As in Example 1, 5 cc of this catalyst were charged to a catalyst evaluation reactor and a gas flow rate and composition the same as in Example 1 were employed.

At a temperature of 530° C. and reaction pressure of 200 psig the exit gas composition on a dry basis was as follows:

|  | Vol. % |
| --- | --- |
| $H_2$ | 17.9 |
| CO | 20.9 |
| $CH_4$ | 46.3 |
| $CO_2$ | 14.9 |

Calculation based on a carbon balance indicates that this exit gas composition corresponds to a CO conversion of 65%. 61% of the CO converted was recovered as methane, the remainder being $CO_2$. This result is rather close to that obtained in Example 1.

EXAMPLE 3

A run similar to Examples 1 and 2 was conducted with a mixture corresponding to a 2/1=S/Mo ratio was employed. The following materials were used to prepare the catalyst.

A solution containing 88 g of $(NH_4)_6Mo_7O_{24}.4H_2O$ in 120 g of distilled water was mixed with a solution containing 76 g of $NH_4CNS$ in 50 g of distilled water and processed further as in Example 1.

The procedure employed for catalyst reduction was similar to that employed in Examples 1 and 2. In this case, 17.1 g of a mixture containing 0.079 g atoms of molybdenum was charged to the reduction reactor. The evolution of $H_2S$ during reduction produced a precipitate of 5.1 g of CdS which is equivalent to 0.04 g at. of S, so in this case only one half an atom of sulfur was removed. However, since only enough sulfur was present in the original mixture to produce $MoS_2$, the removal of this sulfur corresponds to the presence of some molybdenum oxide since hydrogen reduction was not carried out at a sufficiently high temperature to reduce $MoS_2$ to metallic Mo.

As in Examples 1 and 2, 5 cc of the catalyst were charged to a catalytic reaction system employing the same feed gas and reaction conditions as the other two examples.

At a temperature of 530° C. and reaction pressure of 200 psig the exit gas composition on a dry basis was as follows:

|  | Vol. % |
|---|---|
| $H_2$ | 16.6 |
| CO | 20.7 |
| $CH_4$ | 47.0 |
| $CO_2$ | 15.7 |

This corresponds to a 66% conversion of CO with 60% of the converted CO going to $CH_4$, the remainder to $CO_2$. Thus, despite the fact that the catalyst composites corresponded to somewhat less than the $MoS_2$ ratio of S/Mo, the yield was close to that obtained previously.

EXAMPLE 4

Another run was conducted following the procedure of production of $MoS_2$ via ammonium tetrathiomolybdate $(NH_4)_2MoS_4$. The following procedure was employed.

A solution containing 180 g of $(NH_4)_6Mo_7O_{24}.4H_2O$ in 360 g of distilled water was added to 1200 g of $NH_4OH$ (d=0.94) and a rapid stream of $H_2S$ passed through the solution. After completed precipitation the dark red crystals of $(NH_4)_2MoS_4$ were filtered off by suction, washed with ice cold water, alcohol and vacuum dried in a desiccator.

The mass produced upon heating to 300° C. was treated in the same fashion as in the case of Examples 1-3. In this case, the weight of the mass before reduction was 19.9 g corresponding to 0.077 g atoms of molybdenum. The product of CdS due to $H_2S$ evolution was 10.8 g corresponding to 0.07 g at. of elemental sulfur. Thus, in this case enough sulfur was liberated to allow for conversion of $MoS_3$ to $MoS_2$, as was also observed in Example 1 where a 6/1=S/Mo ratio was employed.

As in Examples 1-3, 5 cc of the final catalyst were charged to the catalytic reactor using the same feed gas and process conditions as previously.

At a temperature of 530° C. and reaction pressure of 200 psig the exit gas composition was as follows:

|  | Vol. % |
|---|---|
| $H_2$ | 18.3 |
| CO | 22.5 |
| $CH_4$ | 44.7 |
| $CO_2$ | 14.5 |

This corresponds to a 62% conversion of CO with 60% of the converted CO going to $CH_4$ the remainder to $CO_2$. The result is very similar to that obtained previously, indicating that the procedure using thiocyanate will produce a catalyst of comparable activity, though in some cases the composition cannot correspond to $MoS_2$.

EXAMPLE 5

In this run tungsten was employed in place of molybdenum using the thiocyanate sulfiding procedure.

A solution containing 116 g of $WO_3$ added as ammonium meta tungstate dissolved in 200 g of distilled water was mixed with a solution containing 228 g of $NH_4CNS$ in 150 g of distilled water and processed further as in Example 1.

The mass produced upon heating to 300° C. was treated in the same fashion as in the previous examples, by heating to a temperature of 500° C. for hydrogen reduction.

The catalyst produced was evaluated employing a gas feed with composition as follows:

|  | Vol. % |
|---|---|
| $H_2$ | 46.4 |
| CO | 39.2 |
| $CH_4$ | 13.9 |

The catalyst reactor employed a space velocity of 4800 v/v/hr and a pressure of 200 psig. At a temperature of 530° C. the following dry gas exit composition was as follows:

|  | Vol. % |
|---|---|
| $H_2$ | 24.9 |
| CO | 23.7 |
| $CH_4$ | 38.2 |
| $CO_2$ | 13.2 |

This corresponds to a CO conversion of 57%, 59% of the CO converted yields methane, the remainder produces $CO_2$.

EXAMPLE 6

A catalyst consisting of mixed tungsten and molybdenum oxysulfides in the atomic ratio of Mo/W=1/1 was prepared as follows.

A solution containing 46.4 g of $WO_3$ added as ammonium meta tungstate and 35.2 g of $(NH_4)_6Mo_7O_{24}.4H_2O$ in 150 g of distilled water was mixed with a solution containing 182 g of $NH_4CNS$ in 120 g of distilled water and processed further as in Example 1.

The mass produced upon heating the thiocyanate melt was reduced by hydrogen at a temperature of 550° C. following the previously described procedure.

The product was tested in a catalytic reactor employing a gas feed of the following composition:

|  | Vol. % |
|---|---|
| $H_2$ | 46.0 |
| CO | 37.0 |
| $CH_4$ | 17.0 |
| 2500 ppm of $H_2S$ | |

The product gas corresponding to operation at a temperature of 530° C. was as follows:

|  | Vol. % |
|---|---|
| $H_2$ | 25.7 |
| CO | 20.2 |
| $CH_4$ | 43.9 |
| $CO_2$ | 10.4 |

This analysis corresponds to a conversion of CO of 60%, 67% of the CO converted gas to methane, the remainder to $CO_2$.

EXAMPLE 7

A run was made in which vanadium served as the metal to be reduced by thiocyanate. In this case it is not possible to prepare ammonium thiovanadate and vanadates themselves are not as soluble as tungstates and molybdates. Consequently, the following procedure employing oxalate complex was employed.

A solution containing 70.2 g of $NH_4VO_3$ and 140 g of oxalic acid in 200 g of distilled water was mixed with a solution containing 228 g of $NH_4CNS$ in 120 g of distilled water and processed further as in Example 1.

The mass produced upon decomposition of the thiocyanate melt required a higher reduction temperature of about 650° C. as compared with 500° C. for tungsten and molybdenum catalyst.

The product was tested in a catalytic reactor employing a feed gas of the following composition:

|  | Vol. % |
|---|---|
| $H_2$ | 55.4 |
| CO | 30.7 |
| $CH_4$ | 13.8 |
| 2500 ppm $H_2S$ | |

The gas was fed to the reactor at 200 psig and a feed rate corresponding to 4800 v/v/hr. At a temperature of 530° C. the following dry gas composition product was obtained:

|  | Vol. % |
|---|---|
| $H_2$ | 38.6 |
| CO | 21.6 |
| $CH_4$ | 33.4 |
| $CO_2$ | 6.4 |

This analysis corresponds to a conversion of CO of 49%, with 69% of the CO converted going to $CH_4$, the remainder to $CO_2$.

Even with the usual passivation, the catalyst exhibited some pyrophoric character so it is possible that higher activity might be obtained by a longer passivation period.

EXAMPLE 8

A mixed metal oxide catalyst with an atomic ratio of V/Mo=3/1 was prepared as follows:

A solution containing 70.2 g of $NH_4VO_3$ and 140 g of oxalic acid in 200 g of distilled water was mixed with a solution containing 35.2 g of $(NH_4)_6Mo_7O_{24}.4H_2O$ in 70 g of distilled water; to this mixture was added a solution containing 320 g of $NH_4CNS$ in 150 g of distilled water and the mixed solutions were processed further as in Example 1.

The mass produced was reduced at 650° C. as in the case of the vanadium catalyst of Example 7.

The product was tested in a catalytic reactor employing a feed gas of the following composition:

|  | Vol. % |
|---|---|
| $H_2$ | 55.4 |
| CO | 30.7 |
| $CH_4$ | 13.8 |
| 2500 ppm $H_2S$ | |

This gas was fed to the evaluation reactor at a feed rate corresponding to 4800 v/v/hr and a pressure of 200 psig. At a temperature of 530° C. the following dry gas composite product was obtained:

|  | Vol % |
|---|---|
| $H_2$ | 30.5 |
| CO | 17.2 |
| $CH_4$ | 43.2 |
| $CO_2$ | 9.1 |

This analysis corresponds to a conversion of CO of 64%, with 70% of the Co converted going to methane, the remainder to $CO_2$.

This represents some improvement in yield over a straight vanadium catalyst Example 7. The material was not pyrophoric after passivation.

EXAMPLE 9

In order to test the effect of carbonaceous material, the following catalyst preparation was made in which anthracene was added to the initial formulation.

A solution containing 88 g of $(NH_4)_2Mo_7O_{24}.H_2O$ in 120 g of distilled water was mixed with 114 g of $NH_4CNS$ dissolved in 70 g of distilled water. To this mixture were added 8.0 g of anthracene powder and the mixture was processed further as in Example 1.

The mass produced was heated to 300° C. for about 2 hrs and reduced at 500° C. with hydrogen as previously.

The product was evaluated employing a feed gas of the following composition:

|  | Vol. % |
|---|---|
| $H_2$ | 41.2 |
| CO | 43.3 |
| $CH_4$ | 15.5 |
| 2500 ppm $H_2S$ | |

The gas was fed to a reactor at a rate of 4800 v/v/hr at a pressure of 200 psig. At a temperature of 530° C. the following gas was produced on a dry basis:

|  | Vol. % |
|---|---|
| $H_2$ | 20.3 |
| CO | 22.3 |
| $CH_4$ | 45.4 |
| $CO_2$ | 12.0 |

This corresponds to a 62% overall conversion of CO, the formation of CO converted going to $CH_4$ is 67%, the remainder going to $CO_2$.

This yield is considered very good in view of the fact that a lower $H_2$/CO ratio was present in the feed gas than in the previous examples.

EXAMPLE 10

In this run the effect of addition of silica gel to the catalyst formulation was tested.

A solution of 88 g of $(NH_4)_2Mo_7O_{24}.4H_2O$ in 120 g of distilled water was mixed with 114 g of $NH_4CNS$ dissolved in 70 g of distilled water. To this mixture were added 20 g of "Nalco" silica gel containing 40% of $SiO_2$ and the mixture processed further as in Example 1.

The thiocyanate mass was heated to 300° C. for 2 hours and reduced at 500° C. in the presence of hydrogen.

The catalyst product was tested in the usual evaluation apparatus with a feed gas of the following composition:

|  | Vol. % |
|---|---|
| $H_2$ | 41.2 |
| CO | 43.3 |
| $CH_4$ | 15.5 |
| 2500 ppm $H_2S$ | |

The feed gas was passed to the reactor at a rate of 4800 v/v/hr and a pressure of 200 psig. At a temperature of about 530° C. the following gas was produced on a dry basis:

|  | Vol. % |
|---|---|
| $H_2$ | 19.2 |
| CO | 21.1 |
| $CH_4$ | 42.4 |
| $CO_2$ | 17.3 |

This exit composition corresponds to an overall CO conversion of 65%, with 55% of the methane converted going to $CH_4$ and the remainder to $CO_2$.

EXAMPLE 11

This example shows how small proportions of an additional metal, such as cobalt in this case, can be incorporated in the catalyst.

A solution of 88 g of $(NH_4)_6Mo_7O_{24}.4\ H_2O$ in 120 g of distilled water was mixed with 114 g of $NH_4CNS$ dissolved in 70 g of distilled water. To this mixture were added 1.975 g of $Co(NO_3)_2.6\ H_2O$ dissolved in 20 g of distilled water and the mixture processed further as in Example 1.

The mass produced was heated to 300° C. for 2 hours and reduced at 500° C. in the presence of hydrogen.

The product was evaluated employing a feed gas of the following composition:

|  | Vol. % |
|---|---|
| $H_2$ | 48.2 |
| CO | 37.8 |
| $CH_4$ | 14.0 |
| 2500 ppm $H_2S$ | |

The feed gas was passed to the reactor at a rate of 4800 v/v/hr and at a pressure of 200 psig. At a temperature of about 530° C. the following gas was produced on a dry basis:

|  | Vol. % |
|---|---|
| $H_2$ | 28.0 |
| CO | 23.3 |
| $CH_4$ | 37.4 |
| $CO_2$ | 11.3 |

This corresponds to a 55.7% overall conversion of CO. The proportion of the CO converted going to $CH_4$ is 61.3%, the remainder going to $CO_2$.

EXAMPLE 12

In this example the effect of making a catalyst in which all three active transition elements, V, W and Mo were incorporated into the catalyst.

Solutions of (1) 35.2 g of $(NH_4)_6Mo_7O_{24}.4\ H_2O$ in 70 g of distilled water, (2) 37 g of $WO_3$ (added as ammonium meta tungstate) in 70 g of distilled water, (3) 23.4 g of $NH_4VO_3$ and 47 g of oxalic acid in 70 g of distilled water were mixed and to the mixture was added a solution of 136.8 g of $NH_4CNS$ in 80 g of distilled water. The mixture was processed further as in Example 1.

The mass produced was heated to 300° C. for 2 hours and reduced at 500° C. in the presence of hydrogen. The product was evaluated employing a feed gas of the following composition:

|  | Vol. % |
|---|---|
| $H_2$ | 48.2 |
| CO | 37.8 |
| $CH_4$ | 14.0 |
| 2500 ppm $H_2S$ | |

The feed gas was passed to the reactor at a rate of 4800 v/v/hr and a pressure of 200 psig. At a temperature of about 530° C. the following gas was produced on a dry basis:

|  | Vol. % |
|---|---|
| $H_2$ | 32.0 |
| CO | 23.4 |
| $CH_4$ | 34.0 |
| $CO_2$ | 10.6 |

This corresponds to a 52.9% overall CO conversion with 59.7% of the CO being converted to $CH_4$, the remainder going to $CO_2$.

EXAMPLE 13

In this example the catalyst is prepared by dissolving the molybdenum compound in molten thiocyanate. 88.3 g of $(NH_4)_6Mo_7O_{24}.4\ H_2O$ was thoroughly dry mixed with 114.2 g of $NH_4CNS$. The material was then heated slowly to melt the solids, slowly decomposing and reaching the molten salts until a very viscous melt forms. The hot residue was then heated further in an oven at 300° C. for one hour. The mass was then reduced at 500° C. in the presence of hydrogen.

As in Examples 1–3, 5 cc of the final catalyst were charged to the catalytic reactor using the same experimental conditions. The conversions and yields obtained were similar to those obtained previously.

EXAMPLE 14

In this run the effect of addition of zirconium to the catalyst formulation was tested.

A solution of 88 g of $(NH_4)_2Mo_7O_{24}.4\ H_2O$ in 120 g of distilled water was mixed with 114 g of $NH_4CNS$ dissolved in 70 g of distilled water. To this mixture were added 120 g of zirconium nitrate solution containing 20% by weight of $ZrO_2$ and the mixture processed further as in Example 1.

The thiocyanate mass was heated to 300° C. for 2 hours and reduced at 500° C. in the presence of hydrogen.

The catalyst product was tested in the usual evaluation apparatus with a feed gas of the following composition:

|  | Vol. % |
| --- | --- |
| $H_2$ | 44.3 |
| CO | 39.7 |
| $CH_4$ | 16.0 |
| 2500 ppm $H_2S$ | |

The feed gas was passed to the reactor at a rate of 4800 v/v/hr and a pressure of 200 psig. At a temperature of about 530° C. the following gas was produced on a dry basis:

|  | Vol. % |
| --- | --- |
| $H_2$ | 19.0 |
| CO | 17.4 |
| $CH_4$ | 48.6 |
| $CO_2$ | 15.0 |

This exit composition corresponds to an overall CO conversion of 69.8% with 62.4% of the methane converted going to $CH_4$ and the remainder to $CO_2$.

As indicated above, the basic structure of the catalyst can be varied by the incorporation of additional elements into the original mix enhanced into the final catalyst structure. Additional elements which may be added as support elements include Aluminum, Silicon, Boron, Cerium, Titanium and Zirconium, up to equiatomic proportions of the transition element. Similarly, up to 0.1 atomic proportions of Cobalt, Nickel, Iron or Manganese may be added as promoters. The sulfur may vary from atomic ratios of 1.3 to 3.0 of the transition element, the oxygen from 0 to the upper limit required by the stoichiometry of the system. Carbon and nitrogen can be present up to about 0.1 atom per mole making the formula $$X\ Y_x Z_y S_z O_w C_t N_v$$

where
X is the transition element or a mixture thereof selected from the group V, Mo, W;
Y is a support element or a mixture thereof selected from the group Al, Si, B, Ce, Ti, where x can vary from 0 to 1;
Z is a promoter element or a mixture thereof selected from the group Co, Ni, Fe, Mn, wherein y can vary from 0 to 0.1;
S is the element sulfur where z can vary from 1.3 to 3.0;
O is the element oxygen where w can vary from 0 to the upper limit required by the stoichiometry;
C is the element carbon where t can vary from 0 to 0.1;
N is the element nitrogen where v can vary from 0 to 0.1.

Obviously the examples can be multiplied indefinitely without departing from the scope of the invention as defined in the claim.

What is claimed is:

1. A process for preparing catalysts of the following empirical atomic formula:

$$X\ Y_x Z_y S_z O_w C_t N_v$$

wherein

X is a transition element or a mixture thereof selected from the group V, Mo, W
Y is a support element or a mixture thereof selected from the group Al, Si, B, Ce, Ti, Zr, where x can vary from 0 to 1
Z is a promoter element or mixture thereof selected from the group Co, Ni, Fe, Mn, where y can vary from 0 to 0.1
S is the element sulfur, where z can vary from 1.3 to 3
O is the element oxygen, where w can vary from 0 to the upper limit required by the stoichiometry
C is the element carbon, where t can vary from 0 to 0.1
N is the element nitrogen, where v can vary from 0 to 0.1, which consists in preparing a molten solution of a compound of a transition element X in ammonium thiocyanate and/or thiourea in intimate admixture with compounds to supply other elements of the catalyst, heating said mixture in a non-oxidizing atmosphere to a temperature sufficiently high to drive off gases and to produce a solidified mass, calcining said mass in an inert atmosphere at temperatures sufficiently high to remove hydrogen sulfide or sulfur, further heating in a reducing atmosphere to activate the mass to a product catalyst and cooling said product catalyst in a stream of non-reactive gas.

2. A process for preparation of sulfided catalysts based on one or more elements of the group consisting of tungsten, molybdenum and vanadium in which solutions of non-sulfur containing salts of these metals separately or in mixtures are admixed with solutions of ammonium thiocyanate and/or thiourea, and in which the resultant product is heated to produce a melt which is further heated in a non-oxidizing atmosphere to drive off volatile components, producing a solid mass which is suitable for direct production of granular or pelleted catalysts.

3. A process according to claim 2 in which additional ingredients such as carbon and silica are employed in the mixture of metal salts with ammonium thiocyanate and/or thiourea.

4. The process of claim 1, in which said cooled product catalyst is passivated by treatment with a stream of oxygen and/or water vapor diluted with nitrogen until no exotherm is noted.

5. A process according to claim 2, in which said mixture is initially heated up to a temperature in the range of 200° to 300° C. for a sufficient time to produce a solid mass, said solid mass is placed in an inert or otherwise non-oxidizing atmosphere and further heated to a range of 250° to 450° C. for 2 to 20 hours, the mass is then cooled, crushed and sieved to 30 to 60 mesh size, the resultant particle mixture is then heated to 400° to 600° C. by means of a stream of hot nitrogen, followed by a stream of hot hydrogen which may contain hydrogen sulfide, continuing the heating for a period of time sufficient to remove all extraneous volatile compounds, said particle mixture is then cooled with a stream of cold inert gas, and is then passivated by passing a dilute mixture of oxygen in nitrogen through the catalyst mass until an exotherm is no longer observed.

6. A process according to claim 2 in which, in addition to the metals tungsten, vanadium and molybdenum, up to 0.1 mols of one or more additional metals from the group Ni, Co, Fe and Mn are added, per mol of tungsten, vanadium and molybdenum.

* * * * *